(12) United States Patent
Ambrosio et al.

(10) Patent No.: US 8,852,627 B2
(45) Date of Patent: *Oct. 7, 2014

(54) POROUS BIORESORBABLE ROPE SHAPED WOUND DRESSING COMPRISING MICROPARTICLES AND REDUCED PRESSURE SOURCE

(71) Applicant: KCI Licensing, Inc., San Antonio, TX (US)

(72) Inventors: Archel Ambrosio, San Antonio, TX (US); Joanna Payne, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/942,382

(22) Filed: Jul. 15, 2013

(65) Prior Publication Data
US 2013/0304005 A1 Nov. 14, 2013

Related U.S. Application Data

(62) Division of application No. 13/584,373, filed on Aug. 13, 2012, now Pat. No. 8,496,959, which is a division
(Continued)

(51) Int. Cl.
| | |
|---|---|
| *A61F 13/00* | (2006.01) |
| *A61L 15/00* | (2006.01) |
| *A61L 15/16* | (2006.01) |
| *A61M 1/00* | (2006.01) |
| *A61L 15/42* | (2006.01) |
| *A61L 15/64* | (2006.01) |

(52) U.S. Cl.
CPC ............ *A61M 1/0023* (2013.01); *A61L 15/425* (2013.01); *A61F 13/00987* (2013.01); *A61F 2013/00536* (2013.01); *A61L 15/64* (2013.01); *A61F 2013/00927* (2013.01)
USPC ........... 424/443; 424/444; 424/445; 424/447; 604/304; 604/313; 604/543

(58) Field of Classification Search
None
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Isis Ghali

(57) ABSTRACT

Methods, system and compositions for making and using a bioresorbable linked dressing made of bioresorbable microspheres in various configurations are provided for use in applying reduced pressure to a wound site. The methods include manufacture of a bioresorbable dressing comprising a casing and bioresorbable microspheres in the form of a rope shape. Further, the casing of the dressing comprises pores formed by a porogen system that may be activated by external to the wound or formed in situ within the wound site. The shape of the dressing allows the dressing to be placed into the wound site such that it fills the shape and size of the wound. Embodiments include formation of various rope dressing and their use in conjunction with reduced pressure therapy.

23 Claims, 8 Drawing Sheets

Related U.S. Application Data of application No. 13/355,266, filed on Jan. 20, 2012, now Pat. No. 8,273,368, which is a division of application No. 11/983,549, filed on Nov. 9, 2007, now Pat. No. 8,110,216.

(60) Provisional application No. 60/857,903, filed on Nov. 9, 2006, provisional application No. 60/857,902, filed on Nov. 9, 2006, provisional application No. 60/857,814, filed on Nov. 9, 2006.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,948,575 A | 8/1990 | Cole et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,376,376 A | 12/1994 | Li |
| 5,437,622 A | 8/1995 | Carion |
| 5,437,651 A | 8/1995 | Todd et al. |
| 5,525,646 A | 6/1996 | Lundgren et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,716,413 A | 2/1998 | Walter et al. |
| 5,766,631 A | 6/1998 | Arnold |
| 5,792,469 A | 8/1998 | Tipton et al. |
| 5,863,297 A | 1/1999 | Walter et al. |
| 5,981,568 A | 11/1999 | Kunz et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,562,374 B1 | 5/2003 | Han et al. |
| 6,586,246 B1 | 7/2003 | Yoon et al. |
| 6,689,339 B1 | 2/2004 | Tanaka et al. |
| 6,720,374 B2 | 4/2004 | Sashida et al. |
| 6,814,079 B2 | 11/2004 | Heaton et al. |
| 7,700,819 B2 | 4/2010 | Ambrosio et al. |
| 8,110,216 B2 | 2/2012 | Ambrosio et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0142992 A1 | 10/2002 | Scherr |
| 2002/0143286 A1 | 10/2002 | Tumey |
| 2003/0044380 A1 | 3/2003 | Zhu et al. |
| 2003/0180344 A1 | 9/2003 | Wise et al. |
| 2005/0123590 A1 | 6/2005 | Burton et al. |
| 2006/0055089 A1 | 3/2006 | Zhang et al. |
| 2006/0199876 A1 | 9/2006 | Troczynski et al. |

FOREIGN PATENT DOCUMENTS

| | | |
|---|---|---|
| AU | 755496 | 2/2002 |
| CA | 2005436 | 6/1990 |
| CA | 2547390 A1 | 6/2005 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |

(56) References Cited

FOREIGN PATENT DOCUMENTS

| GB | 2 333 965 A | 8/1999 |
|---|---|---|
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), Vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. Đukić, Ž, Maksimović, Đ. . Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

POROUS BIORESORBABLE ROPE SHAPED WOUND DRESSING COMPRISING MICROPARTICLES AND REDUCED PRESSURE SOURCE

CROSS-REFERENCE TO RELATED APPLICATIONS

This application is a divisional of U.S. application Ser. No. 13/584,373, filed Aug. 13, 2012, which is a divisional of U.S. application Ser. No. 13/355,266, filed Jan. 20, 2012, issued as U.S. Pat. No. 8,273,368, on Sep. 25, 2012, which is a divisional of U.S. application Ser. No. 11/983,549, filed Nov. 9, 2007, issued as U.S. Pat. No. 8,110,216, on Feb. 7, 2012, which claims the benefit of U.S. Provisional Application No. 60/857,903, filed Nov. 9, 2006, U.S. Provisional Application No. 60/857,902, filed Nov. 9, 2006, and U.S. Provisional Application No. 60/857,814, filed Nov. 9, 2006. Priority is claimed to all of the above-mentioned applications, and each application is hereby incorporated by reference.

BACKGROUND OF THE INVENTION

1. Field of the Invention

The present invention relates generally to methods, systems and compositions for making and using a porous bioresorbable dressing comprising bioresorbable microspheres for use in conjunction with reduced pressure wound therapy.

2. Description of Related Art

Wound healing may be broadly split into three overlapping basic phases: inflammation, proliferation, and maturation. The inflammatory phase is characterized by hemostasis and inflammation. The next phase consists mainly of epithelialization, angiogenesis, granulation tissue formation, and collagen deposition. The final phase includes maturation and remodeling. The complexity of the three step wound healing process is augmented by the influence of local factors such as ischemia, edema, and infection, and systemic factors such as diabetes, age, hypothyroidism, malnutrition, and obesity. The rate limiting step of wound healing, however, is often angiogenesis. Wound angiogenesis is marked by endothelial cell migration and capillary formation where the sprouting of capillaries into the wound bed is critical to support the regenerating tissue. The granulation phase and tissue deposition require nutrients supplied by the capillaries. Impairments in wound angiogenesis therefore may lead to chronic problem wounds.

Expression of the angiogenic phenotype is a complex process that requires a number of cellular and molecular events to occur in sequential steps. Some of these activities include endothelial cell proliferation, degradation of surrounding basement membrane, migration of endothelial cells through the connective tissue stroma, formation of tube-like structures, and maturation of endothelial-lined tubes into new blood vessels. Angiogenesis is controlled by positive and negative regulators. In addition to endothelial cells, cells associated with tissue repair, such as platelets, monocytes, and macrophages, release angiogenic growth factors, such as vascular endothelial growth factor (VEGF) into injured sites that initiate angiogenesis.

There are currently several methods used to augment wound healing, including irrigating the wound to remove of toxins and bacteria, local and systemic antibiotics and anesthetics, and local application of growth factors. One of the most successful ways to promote wound healing in soft tissue wounds that are slow to heal or non-healing is reduced pressure therapy. Reduced pressure therapy generally refers to application of a pressure less than the ambient pressure at the wound site, where the magnitude and time period of the reduced pressure treatment is sufficient to promote healing or tissue growth. Examples of devices used to apply reduced pressure include those popularized by Kinetic Concepts, Inc. of San Antonio, Tex., by its commercially available VACUUM ASSISTED CLOSURE® or V.A.C.® product line. The reduced pressure induced healing process has been described in U.S. Pat. Nos. 5,636,643 and 5,645,081, the disclosures of which are incorporated fully by reference.

The reduced pressure serves to promote the migration of epithelial tissue and subcutaneous tissue from the healthy tissue towards the wound site. Typical reduced pressure therapy includes application of reduced pressure to a wound site through a dressing that serves as a manifold to distribute the reduced pressure. The dressing is sized to fit the existing wound, placed in contact with the wound, and then periodically replaced with smaller pieces of dressing as the wound begins to heal and becomes smaller. While use of reduced pressure therapy with the dressing has been highly successful, there still exists various difficulties with this process. For example, it may be difficult to obtain a dressing of a proper width, length or depth to properly fit the wound. Further, as the dressing is removed it may also remove healthy tissue, thereby causing further trauma to the wound site.

It has been proposed to use biodegradable materials to make the dressing, thereby resulting in a dressing that need not be removed from the wound site. With many of these dressings, however, the biodegradable polymer is formed in advance into a particular shape. Individual wounds, however, are of inconsistent shapes and sizes.

A need exists, therefore, for a dressing that be easily manufactured and configured to a shape and size to fit the individual patient's wound. A need also exists for a dressing that need not be removed from the wound site. Further, a need exists for a dressing that contains pores such that the dressing can promote healing and healthy tissue growth at the wound site by inducing granulation tissue formation.

All references cited herein are incorporated by reference to the maximum extent allowable by law. To the extent a reference may not be fully incorporated herein, it is incorporated by reference for background purposes and indicative of the knowledge of one of ordinary skill in the art.

BRIEF SUMMARY OF THE INVENTION

These and other needs are met through the use of a rope shaped bioresorbable dressing containing bioresorbable microspheres. The configuration allows the dressing to readily conform to the size and shape of any wound site. Further, because the dressing is bioresorbable, it does not have to be removed from the wound site. Thus, in its broadest sense, the invention produces methods, systems and compositions for making and using a bioresorbable dressing made of bioresorbable microspheres in various configurations.

One embodiment in accordance with the invention is a method for making a bioresorbable dressing to be used at a wound site undergoing reduced pressure therapy. In this embodiment, at least one bioresorbable polymer is dissolved in an appropriate solvent. The polymer mixture is then sprayed, dip coated or poured over a cylinder and the residual solvent is removed. The resulting cylindrically-shaped biodegradable polymer is then filled with bioresorbable microspheres. The cylinder is constricted at regular, repeating intervals to form a rope shaped dressing.

Another embodiment in accordance with the invention is a method for making a porous bioresorbable dressing to be used at a wound site undergoing reduced pressure therapy. In this embodiment, at least one bioresorbable polymer is dissolved in an appropriate solvent and mixed with a porogen. The polymer mixture is then sprayed, dip coated or poured over a cylinder and the residual solvent is removed. The resulting cylindrical shaped biodegradable polymer is then filled with bioresorbable microspheres. The casing is constricted at regular, repeating intervals to form a rope shaped dressing.

Another embodiment in accordance with the invention is a method for making a porous bioresorbable dressing to be used at a wound site undergoing reduced pressure therapy. In this embodiment, at least one bioresorbable polymer is dissolved in an appropriate solvent and mixed with a porogen. The polymer mixture is then sprayed, dip coated or poured over a cylinder and the residual solvent is removed. The resulting cylindrically-shaped biodegradable polymer, i.e., casing, is then exposed to a fluid which reacts with the porogen in the casing, creating pores. The casing is filled with bioresorbable microspheres. The casing is then constricted at regular, repeating intervals to form a rope shaped dressing.

One embodiment in accordance with the invention is a method for making a bioresorbable dressing to be used at a wound site undergoing reduced pressure therapy. In this embodiment, at least one bioresorbable polymer is dissolved in an appropriate solvent. The polymer mixture is then extruded into a non-solvent, whereby the polymer mixture precipitates out of solution. The residual non-solvent is removed. The resulting two dimensional sheet of biodegradable polymer is then rolled into a cylindrical shape to form a casing. The cylindrical casing is filled with bioresorbable microspheres and constricted at regular, repeating intervals to form a rope shaped dressing.

Another embodiment in accordance with the invention is a method for making a porous bioresorbable dressing to be used at a wound site undergoing reduced pressure therapy. In this embodiment, at least one bioresorbable polymer is dissolved in an appropriate solvent and mixed with a porogen. The resulting polymer mixture is then extruded onto the surface of a non-solvent, whereby the polymer mixture precipitates out of solution, The residual non-solvent is removed. The resulting two dimensional sheet of biodegradable polymer is then rolled into a cylindrical shape to form a casing. The cylindrical casing is filled with bioresorbable microspheres and then constricted at regular, repeating intervals to form a rope shaped dressing.

Another embodiment in accordance with the invention is a method for making a porous bioresorbable dressing to be used at a wound site undergoing reduced pressure therapy. In this embodiment, at least one bioresorbable polymer is dissolved in an appropriate solvent and mixed with a porogen. The resulting polymer mixture is then extruded onto the surface of a non-solvent, whereby the polymer mixture precipitates out of solution. The residual non-solvent is removed. The resulting two dimensional sheet of biodegradable polymer is then rolled into a cylindrical shape to form a casing. The resulting casing is exposed to a fluid which reacts with the porogen in the casing, creating pores. The porous casing is then filled with bioresorbable microspheres. The casing is constricted at regular, repeating intervals to form a rope shaped dressing.

In yet another embodiment in accordance with the invention, a reduced pressure delivery system for applying reduced pressure tissue treatment to a wound site is provided, the system including a bioresorbable dressing comprising bioresorbable microspheres. In this embodiment, a bioresorbable dressing is formed by dissolving at least one bioresorbable polymer in an appropriate solvent. The resulting polymer mixture is then formed into a cylindrical shape by any means, including but not limited to, dip coating, spraying or pouring the polymer mixture over a cylinder, or by extruding the polymer mixture onto the surface of a non-solvent to form a two dimensional polymer sheet that is rolled into a cylindrical shape. The cylindrical casing is filled with bioresorbable microspheres and then constricted at regular, repeating intervals to form a rope shaped dressing. The dressing is then placed into the wound site to fit the shape and size of the wound. The system may further include a manifold placed over the dressing and fluidly connected to a reduced pressure delivery tube. The reduced pressure delivery tube is placed in fluid communication with a reduced pressure source.

In yet another embodiment in accordance with the invention, a reduced pressure delivery system for applying reduced pressure tissue treatment to a wound site is provided, the system including a bioresorbable dressing comprising bioresorbable microspheres. In this embodiment, a bioresorbable dressing is formed by dissolving at least one bioresorbable polymer in an appropriate solvent. The resulting polymer mixture is then formed into a cylindrical shape by any means, including but not limited to, dip coating, spraying or pouring the polymer mixture over a cylinder, or by extruding the polymer mixture onto the surface of a non-solvent to form a two dimensional polymer sheet that is rolled into a cylindrical shape. The cylindrical casing is filled with bioresorbable microspheres and then constricted at regular, repeating intervals to form a rope shaped dressing. The dressing is placed into the wound site to fit the shape and size of the wound. The system further includes a manifold placed over the dressing and fluidly connected to a reduced pressure delivery tube. The reduced pressure delivery tube is further placed in fluid communication with a reduced pressure source.

In yet another embodiment in accordance with the invention, a method for promoting new tissue growth and/or healing at a wound site is provided. The method includes preparing a rope-shaped bioresorbable dressing comprising bioresorbable microspheres. The dressing is then placed into the wound site to fit the shape and size of the wound by means of, for example, coiling within the wound. The method includes positioning a manifold over the dressing, connecting the manifold to a reduced pressure delivery tube. A reduced pressure is applied to the wound site through the bioresorbable dressing and the manifold.

In still another embodiment in accordance with the invention, a method for promoting new tissue growth and/or healing at a wound site is provided. The method includes preparing a rope-shaped porous bioresorbable dressing comprising bioresorbable microspheres. The dressing is then placed into the wound site to fit the shape and size of the wound. The method includes positioning a manifold over the dressing, connecting the manifold to a reduced pressure delivery tube. A reduced pressure is applied to the wound site through the bioresorbable dressing and the manifold.

In still another embodiment in accordance with the invention, a method for promoting new tissue growth and/or healing at a wound site is provided. The method includes preparing a rope-shaped porous bioresorbable dressing comprising bioresorbable microspheres. The bioresorbable dressing is first formed by dissolving at least one bioresorbable polymer and a porogen in an appropriate solvent. The resulting polymer mixture is then formed into a cylindrical shape by any means, including but not limited to, dip coating, spraying or pouring the polymer mixture over a cylinder, or by extruding the polymer mixture into a non-solvent to form a two dimensional polymer sheet that is rolled into a cylindrical shape.

The casing is exposed to a fluid which reacts with the porogen in the casing, creating pores. The porous casing is then filled with bioresorbable microspheres and constricting at regular intervals. The dressing is then placed into the wound site to fit the shape and size of the wound. The method includes positioning a manifold over the dressing, connecting the manifold to a reduced pressure delivery tube. A reduced pressure is applied to the wound site through the bioresorbable dressing and the manifold.

In yet another embodiment of the invention, a tissue growth and/or healing kit is provided for promoting new tissue growth at a wound site. The tissue growth kit includes a rope-shaped bioresorbable dressing comprising bioresorbable microspheres, a manifold adapted to contact the dressing, and a reduced pressure device.

In another embodiment in accordance with the invention, a mold and method for its use to prepare a bioresorbable dressing comprising bioresorbable microspheres is provided. The mold includes craters on one face where the craters are of a size such that microspheres may be placed within to form capsules. Embodiments include use of bioresorbable sutures to link the capsules.

Other objects, features, and advantages of the present invention will become apparent with reference to the drawings and detailed description that follow.

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined.

All embodiments of the invention include use of a bioresorbable dressing to be used in conjunction with reduced pressure therapy for treatment of a wound site. The invention is not necessarily limited by a specific location of the wound site, nor the type of tissue that is the target of reduced pressure therapy. Thus, the wound site treated by the instant invention may be a location upon or within the body in which it is desired to promote growth and/or healing of the tissue.

Figure 1:
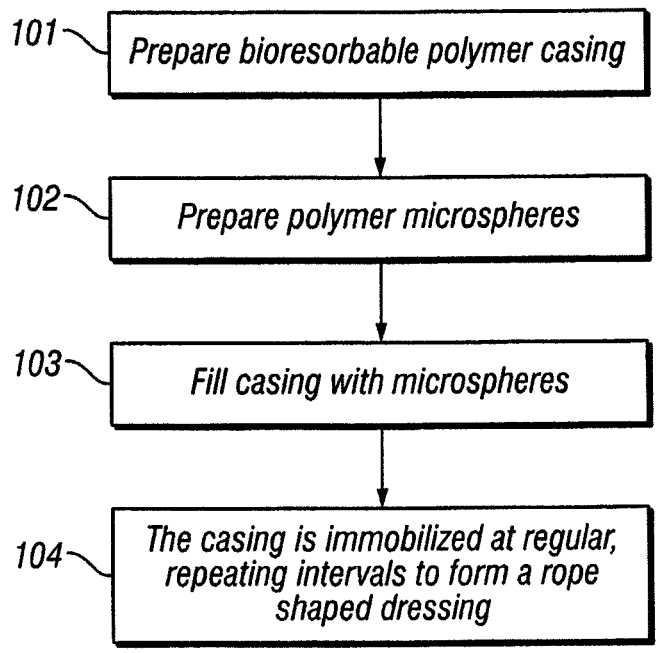
FIG. 1 illustrates a flowchart in accordance with some embodiments of the invention, demonstrating the process of making a dressing comprising a bioresorbable casing and bioresorbable microspheres.

The first embodiment in accordance with the invention is to a method for preparing a bioresorbable dressing that can be placed into a wound of any size, shape or depth and be able to fill the wound completely because of its rope configuration, as illustrated in FIG. 1. The dressing may be used to facilitate tissue growth and/or healing.

The method includes forming a casing by use of one or more bioresorbable polymers (101). The bioresorbable polymer may be a biocompatible material whose degradation by products can be bio assimilated or excreted via natural pathways in the body. The bioresorbable polymer may include, but is not limited to, lactide, poly(lactide) (PLA), glycolide polymers, poly(glycolic acid) (PGA), poly(lactide-co-glycolide) (PLGA), ethylene glycol/lactide copolymers, polycaprolactone (PCL), polyhydroxybutyrate, polyurethanes, polyphosphazenes, poly(ethylene glycol)-poly(lactide-co-glycolide) co-polymer, polyhydroxyacids, polycarbonates, polyamides, polyanhydrides, polyamino acids, polyortho esters, polyacetals, degradable polycyanoacrylates, polycarbonates, polyfumarates, degradable polyurethanes, proteins such as albumin, collagen, fibrin, synthetic and natural polyamino acids, polysaccharides such as alginate, heparin, and other naturally occurring biodegradable polymers of sugar units. Further, in one preferred embodiment the polymer is a PLA:PCL copolymer, wherein the ratio of PLA to PCL may range from 100:0 to 0:100. In some preferred embodiments, the PLA:PCL copolymer ratio is about 90:10. In other embodiments, the PLA:PCL copolymer ratio is about 80:20. In yet another embodiment, the PLA:PCL copolymer ratio is about 70:30.

The one or more bioresorbable polymers is dissolved in an appropriate solvent. The type of solvent used will depend upon the bioresorbable polymer(s) selected. The polymer mixture is then formed into the shape of cylinder by, for example, spraying, dip coating or pouring the polymer mixture over a cylinder and removing the residual solvent. Examples of methods to remove the solvent include, but are not limited to, evaporation, oven drying, vacuum drying and the like. In one embodiment, the solvent is evaporated over a period of about 48 hours.

In an alternate embodiment, one or more plasticizers is added to the bioresorbable polymer in the solvent. Plasticizers may be any materials that enhances the deformability of a polymeric compound, adding softening and flexibility to the compound. The plasticizers may include, but are not limited to, cetyl alcohol esters, glycerol, glycerol esters, acetylated glycerides, glycerol monostearate, glyceryl triacetate, glycerol tributyrate, phthalates, dibutyl phthalate, diethyl phthalate, dimethyl phthalate, dioctyl phthalate, citrates, acetyl tributyl citrate, acetyl triethyl citrate, tributyl citrate, triethyl citrate, sebacates, diethyl sebacate, dibutyl sebacate, adipates, azelates, benzoates, vegetable oils, fumarates, diethyl fumarate, malates, diethyl malate, oxalates, diethyl oxalate, succinates, dibutyl succinate, butyrates, cetyl alcohol esters, salicylic acid, triacetin, malonates, diethyl malonate, castor oil, triethylene glycol, and poloxamers.

If one or more plasticizers are included in the polymer, then the residual solvent may be removed by any method such as oven drying or vacuum drying as long as the conditions used do not favor evaporation of the plasticizer.

Bioresorbable polymer microspheres are then formed (102). The bioresorbable polymer microspheres may be of any size that best suits the needs of the practitioner. While microspheres are substantially spherical in shape, microparticles of other shapes could also be formed. The microparticles may be rectangular parallelepiped, cylindrical, rod-shaped, cuboidal, irregular, or any other shape. Further, the bioresorbable microparticles may contain growth inducing or healing agents such as Bone Morphogenic Protein, Fibroblast Growth Factor, Transforming Growth Factor-β, antibacterial agent, antiviral agent, cell-growth promotion agent, or other chemically active agents. Further, the growth inducing or healing agents may be synthetic or naturally produced, and may be a fragment, derivative or analog of a growth inducing or healing agent.

For all embodiments contemplated, the microparticles may be prepared by any means convenient to the practitioner. For example, the microparticle preparation method may be a spraying method, as seen in U.S. Pat. No. 6,238,705, which is hereby incorporated by reference. Further, the preparation method may be use of an oil/water emulsion method for preparing such polymeric microparticles, such as an oil-in-water or water-in-oil or oil-in-oil emulsion method. The microparticles may also be formed by methods including use of an aqueous two phase method has been applied to prepare polymeric microparticles, such as that disclosed in Gehrke et al. (Proceed. Intern. Symp. Control Rel. Bioact. Material., 22, 145-146), which is hereby incorporated by reference. Preferably, an oil-in-water/emulsion and evaporation method is used to form microparticles. In the oil-in-water emulsion method, the at least one bioresorbable polymer is dissolving in a solvent to form a first mixture. The polymer mixture is then added to an aqueous solution, preferably containing a surfactant, and vigorously agitated by, for example, stirring. The solvent is then evaporated off, leaving resulting microparticles such as microspheres.

If the microparticles are made by emulsion, then the diameter of the microparticles is dependent upon the concentration of the polymer and the level of agitation. Further, the size of the microparticles may be controlled by sieving the microspheres. If microspheres are being formed, the microspheres may be from about 20 to about 1,500 microns in size. Preferably, the microspheres have a diameter in the range of about 20 to about 800 microns range, and more preferably about 400 microns to about 600 microns. For non-spherical microparticles, similarly sized particles are preferred.

The substantially cylindrically-shaped biodegradable polymer, or casing, is then filled with bioresorbable microparticles or microspheres (103). The casing may be constricted at regular, repeating intervals to form a rope shaped dressing. Alternatively, the constrictions may be disposed irregularly along the casing. The constrictions may be formed by twisting, application of heat, solvents, or any other means of constricting the casing (104).

Figure 2:
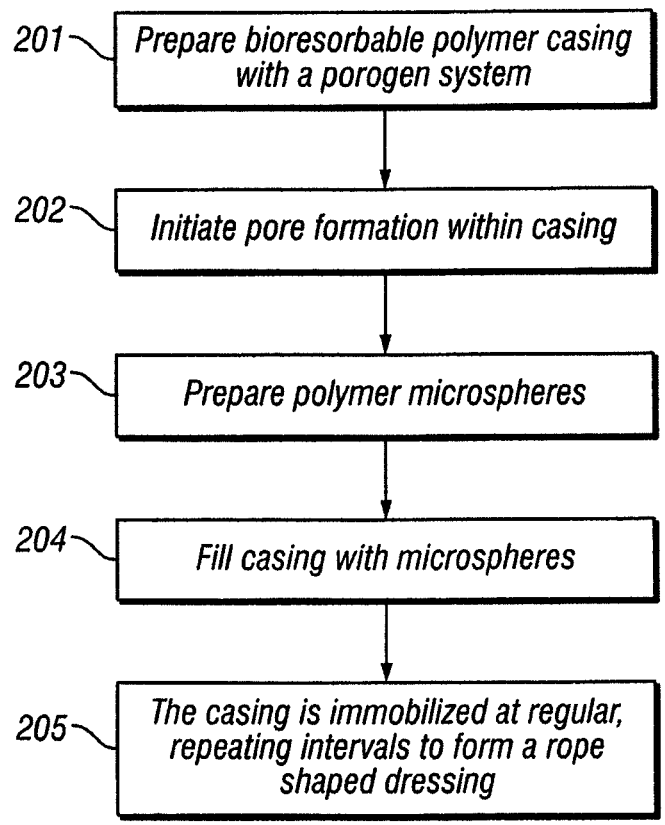
FIG. 2 illustrates a flowchart in accordance with some embodiments of the invention, demonstrating a process of making a porous bioresorbable dressing comprising bioresorbable microspheres.

A second embodiment in accordance with the invention is to a method for preparing a porous bioresorbable dressing that can be placed into a wound of any size, shape or depth and be able to fill the wound completely because of its rope configuration, as illustrated in FIG. 2. The dressing may be used to facilitate tissue growth and/or healing.

The method includes forming a casing by use of one or more bioresorbable polymers and a porogen system (201). To start, one or more bioresorbable polymers is dissolved in an appropriate solvent. The type of solvent used will depend upon the bioresorbable polymer(s) selected. The bioresorbable polymer may include, but is not limited to, lactide, poly (lactide) (PLA), glycolide polymers, poly(glycolic acid) (PGA), poly(lactide-co-glycolide) (PLGA), ethylene glycol/lactide copolymers, polycaprolactone (PCL), polyhydroxybutyrate, polyurethanes, polyphosphazenes, poly(ethylene glycol)-poly(lactide-co-glycolide) co-polymer, polyhydroxyacids, polycarbonates, polyamides, polyanhydrides, polyamino acids, polyortho esters, polyacetals, degradable polycyanoacrylates, polycarbonates, polyfumarates, degradable polyurethanes, proteins such as albumin, collagen, fibrin, synthetic and natural polyamino acids, polysaccharides such as alginate, heparin, and other naturally occurring biodegradable polymers of sugar units. Further, in one preferred embodiment the polymer is a PLA:PCL copolymer, wherein the ratio of PLA to PCL may range from 100:0 to 0:100. In some preferred embodiments, the PLA:PCL copolymer ratio is about 90:10. In other embodiments, the PLA:PCL copolymer ratio is about 80:20. In yet another embodiment, the PLA:PCL copolymer ratio is about 70:30.

A porogen system is then added to the bioresorbable polymer mixture. The porogen system may include one or more compounds that is capable of creating pores within the casing. The type of porogen system is not limited, and may include compounds that dissolve when placed in contact with a fluid. This type of porogen system includes inorganic salts like sodium chloride, crystals of saccharose, or gelatin spheres will dissolve in fluids such as water. Another type of porogen system is a mixture of sodium bicarbonate and an acid. Sodium bicarbonate and acid, when placed in contact with a fluid, result in the bicarbonate and acid reacting to form carbon dioxide gas. The gas may then increase the size of the pores. The amount of porogen system used may be used in stoichiometric amounts. It is also envisioned that the porogen system may be used in non stoichiometric amounts.

In one embodiment, the porogen system is sodium carbonate and an acid. The acid may be any acid that is not in liquid or gaseous form, thus being in a solid or crystalline state. Examples of appropriate acids to use therein include, but are not limited to, citric acid.

In an alternate embodiment, the porogen system is a salt. The invention is not limited by the type of salt, as long as the salt is of an appropriate particle size and dissolvable in a fluid, i.e., a gas, liquid, or flowable material, including but not limited to, colloids, dressings, a liquid, a slurry, a suspension, a viscous gel, a paste, a putty, and particulate solids. Examples of appropriate salts used herein include, but are not limited to, sodium chloride and potassium chloride.

The polymer mixture is then formed into the shape of a cylinder by, for example, spraying, dip coating or pouring the polymer mixture over a cylinder and removing residual solvent. Examples of methods to remove the solvent include, but are not limited to, evaporation, oven drying, vacuum drying and the like. In one embodiment, the solvent is evaporated over a period of about 48 hours.

In an alternate embodiment, one or more plasticizers is added to the bioresorbable polymer in the solvent. If one or more plasticizers are included in the polymer, then the residual solvent may be removed by any method such as oven drying or vacuum drying as long as the conditions used do not favor evaporation of the plasticizer.

The dressing is then placed in warm water to initiate the creation of the pores (202). The resulting spaces left by the porogen system result in a casing with interconnected pores. The size of the resulting pores is dependent upon the size of the porogen particles used. As such, one may use any method to control the size of the porogen system particles, including but not limited to sieving and centrifugation. In one embodiment, the porogen system are sieved through one or more screens to produce particles of a certain size. Thus, the pore size will be at a minimum the size produced by the screen.

Typically, the pore size produced by the porogen system is about 5 to 1,500 microns. In one embodiment, the pore size is between about 100 and about 500 microns. In another embodiment, the pore size is between about 100 and about 250 microns. Further, the amount of porogen system used and the particle size of the porogen system will control the percent porosity. In one preferred embodiment, the percent porosity is at least about 50%. In another preferred embodiment, the percent porosity is about 70%. In yet preferred embodiment, the percent porosity is at least about 90%.

Bioresorbable polymer microparticles, or in one example microspheres, are then formed (203). The microspheres may be prepared by any means convenient to the practitioner. For example, the microsphere preparation method may be a spraying method, as seen in U.S. Pat. No. 6,238,705. Further, the preparation method may be use of an oil/water emulsion method for preparing such polymeric microspheres, such as an oil-in-water or water-in-oil or oil-in-oil emulsion method. The microspheres may also be formed by methods including use of an aqueous two phase method has been applied to prepare polymeric microspheres, such as that disclosed in Gehrke et al. (Proceed. Intern. Symp. Control Rel. Bioact. Material., 22, 145-146). Preferably, an oil-in-water/emulsion and evaporation method is used to form microparticles. In the oil-in-water emulsion method the at least one bioresorbable polymer is dissolving in a solvent to form a first mixture. The polymer mixture is then added to an aqueous solution, preferably containing a surfactant, and vigorously agitated. The solvent is then evaporated off, leaving resulting microspheres.

The bioresorbable polymer microspheres may be of any size that best suits the needs of the practitioner. While microspheres are substantially spherical in shape, microparticles of other shapes may also be formed. The microparticles may be rectangular parallelepiped, cylindrical, rod-shaped, cuboidal, irregular, or any other shape. Further, the bioresorbable microparticles may contain growth inducing or healing agents such as an antibacterial agent, antiviral agent, cell-growth promotion agent, Fibroblast Growth Factor, Transforming Growth Factor-β, or other chemically active agents. Further, the growth inducing or healing agents may be synthetic or naturally produced, and may be a fragment, derivative or analog of a growth inducing or healing agent.

If an emulsion method is used to form the microspheres, then the diameter of the microspheres is dependent upon the concentration of the polymer and the level of agitation. The diameter of the microspheres may also be further controlled by use of screens to sieve the microspheres. It is desired that the diameter of the microspheres be such that the pores from the casing are smaller than the microsphere diameter. It is undesirable to have the diameter of the microsphere be smaller than the casing pore size because the microspheres will not stay within the casing. Preferably, the microspheres have a diameter in the range of about 20 to about 800 microns range, more preferably about 400 microns to about 600 microns. For non-spherical microparticles, similarly sized particles are preferred.

The cylindrical shaped biodegradable polymer, i.e., casing, is then filled with bioresorbable microspheres (204). The casing is constricted at regular, repeating intervals to form a rope shaped dressing. The constriction may occur by twisting, use of heat, solvent, or the like (205). In general, constriction of the casing reduces the diameter or width of the casing in the area of the constriction. This provides additional flexibility along the length of the casing. Since the casing may be easily bent, folded, and otherwise manipulated due to the presence of the constrictions, the casing is capable of easily adapting to fit within a wound or tissue site of any shape.

Figure 3:
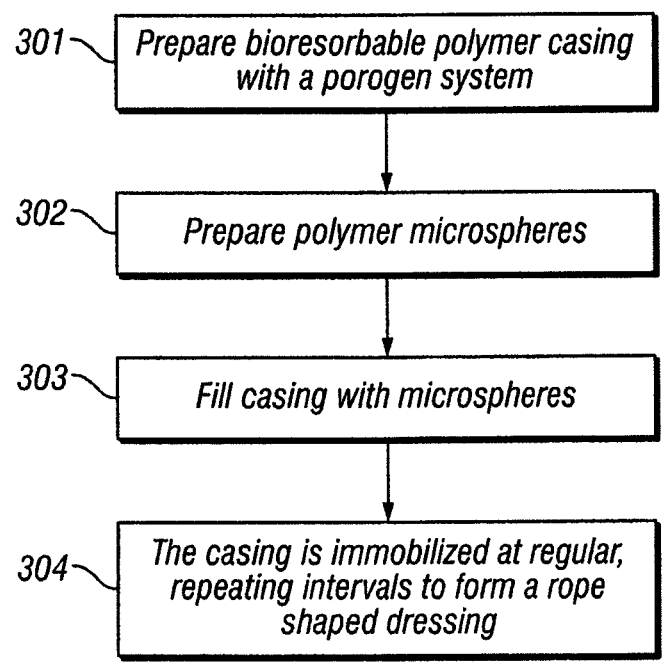
FIG. 3 illustrates a flowchart in accordance with some embodiments of the invention, demonstrating a process of making a porous bioresorbable dressing comprising microspheres, where the porogen system is activated in vivo when the dressing is placed in contact with the wound fluids.

A third embodiment in accordance with the invention is a method for preparing a porous bioresorbable dressing that can be placed into a wound of any size, shape or depth and be able to fill the wound completely because of its rope configuration, where the porogen system is activated in vivo when the dressing is placed in contact with the wound fluids, which may include interstitial liquid in the tissues or liquid that has exuded from the tissue or its capillaries of the wound site. The method of making the dressing is illustrated in FIG. 3. The dressing may be used to facilitate tissue growth and/or healing.

The method includes forming a casing by use of one or more bioresorbable polymers and a porogen system (301). To start, one or more bioresorbable polymers is dissolved in an appropriate solvent. The type of solvent used will depend upon the bioresorbable polymer(s) selected. A porogen system is then added to the bioresorbable polymer mixture. The amount of porogen system used may be used in stoichiometric amounts. It is also envisioned that the porogen system may be used in non stoichiometric amounts. The polymer mixture is then sprayed, dip coated or poured over a cylinder and the residual solvent is removed. Examples of methods to remove the solvent include, but are not limited to, evaporation, oven drying, vacuum drying and the like. In one embodiment, the solvent is evaporated over a period of about 48 hours.

In an alternate embodiment, one or more plasticizers is added to the bioresorbable polymer in the solvent. If one or more plasticizers are included in the polymer, then the residual solvent may be removed by any method such as oven drying or vacuum drying as long as the conditions used do not favor evaporation of the plasticizer.

Bioresorbable polymer microspheres are then formed (302). The bioresorbable microspheres may be prepared by any means convenient to the practitioner. Further, the bioresorbable polymer microspheres may be of a size that best suits the needs of the practitioner. While microspheres are substantially spherical in shape, microparticles of other shapes could also be formed. The microparticles may be rectangular parallelepiped, cylindrical, rod-shaped, cuboidal, irregular, or any other shape. Growth inducing or healing agents may also be included with the microparticles, such as an antibacterial agent, antiviral agent, cell-growth promotion agent, or other chemically active agents. Further, the growth inducing or healing agents may be synthetic or naturally produced, and may be a fragment, derivative or analog of a growth inducing or healing agent.

If emulsion is used to form the microspheres, then the diameter of the microspheres is dependent upon the concentration of the polymer and the level of agitation. The microspheres may also be sieved through screens to control their diameter. It is desired that the diameter of the microspheres be such that the pores from the casing is smaller than the microsphere diameter. It is also desired that the diameter of the microspheres be such that the microsphere packing within the casing does not impede the flexibility of the resulting dressing. Preferably, the microspheres have a diameter in the range of about 20 to about 800 microns range, more preferably about 400 microns to about 600 microns. For non-spherical microparticles, similarly sized particles are preferred.

The cylindrically-shaped biodegradable polymer, or casing, is then filled with bioresorbable microspheres (303). The casing is constricted at regular, repeating intervals to form a rope-shaped dressing. The constriction can occur by twisting, use of heat, solvent, or the like (304). The dressing formed by this method is also novel because the porogen system is activated in vivo when the dressing is placed in contact with the wound fluids.

Figure 4:
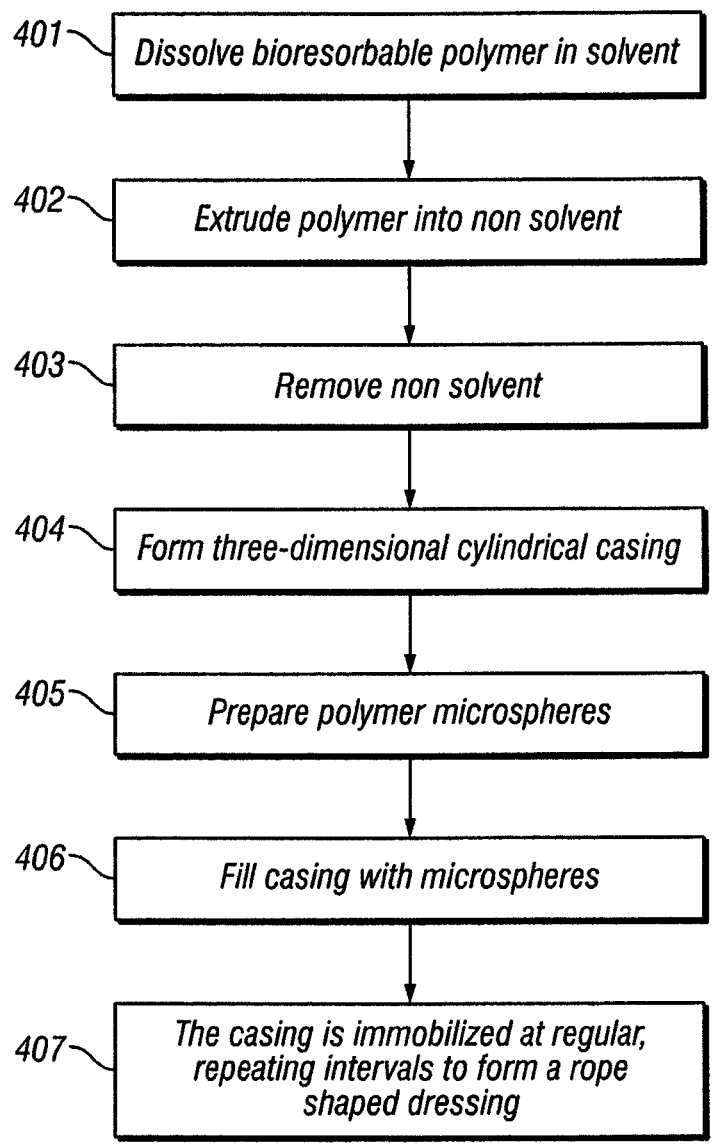
FIG. 4 illustrates a flowchart in accordance with some embodiments of the invention, demonstrating a process of making a bioresorbable dressing comprising bioresorbable microspheres, where the dressing is made by extruded polymer.

A fourth embodiment in accordance with the invention is to a method for preparing a bioresorbable dressing that can be placed into a wound of any size, shape or depth and be able to fill the wound completely because of its rope configuration, where the dressing is made by extruded polymer. The method of making the dressing is illustrated in FIG. 4. The dressing may be used to facilitate tissue growth and/or healing.

A bioresorbable polymer is dissolved in an appropriate solvent to form a non-solid mixture, such as a fluid or slurry, to form a mixture (401). Suitable polymers include, but are not limited to, polymers disclosed in the other embodiments of the invention. Further, the type of solvent used will depend upon the bioresorbable polymer(s) selected. In an alternate embodiment, the bioresorbable polymer is then mixed with one or more plasticizers.

The resulting mixture is then extruded into a non-solvent for the polymer such that the mixture precipitates out of solution when the polymer comes in contact with the non-solvent (402). The residual non-solvent is removed (403). Examples of methods to remove the solvent include, but are not limited to, evaporation, oven drying, vacuum drying and the like. If one or more plasticizers is included in the mixture, then oven drying or vacuum drying may also be used as long as the conditions used do not favor evaporation of the plasticizer. If the polymer sheet contains undesired bubbles or an uneven thickness, the resultant polymer may be heat pressed or compressed.

The resulting flat, two-dimensional sheet of biodegradable polymer is then formed into a three dimensional casing by rolling the sheet into a cylinder shape and gluing the distal touching edges (404). Methods of gluing may include heat welding, chemical gluing, physical crimping, or any other means as long as edges are secured together to form the cylindrical shape. Further, the two-dimensional sheet may be cut or manipulated to better form the three dimensional casing. For example, in one embodiment the sheet may have two ends patterned such that they are compatible for gluing or welding together. In another embodiment, the two-dimensional sheet is cut so that it has one edge having one or more slots and tongues comprising a catch or locking mechanism proximate the longitudinal edge thereof. The cylindrical casing is formed by inserting a portion of the tongue through the slot to provide a cylindrical casing. Further, the edges may be sealed by gluing.

Bioresorbable polymer microspheres are then formed (405). The microspheres may be prepared by any means convenient to the practitioner. The diameter of the microspheres is preferably in the range of about 20 to about 800 microns range, more preferably about 400 microns to about 600 microns.

The cylindrical shaped biodegradable polymer, or casing, is then filled with bioresorbable microspheres (406). The casing is constricted at regular, repeating intervals to form a rope-shaped dressing. The constriction can occur by twisting, use of heat, solvent, or the like (407).

Figure 5:
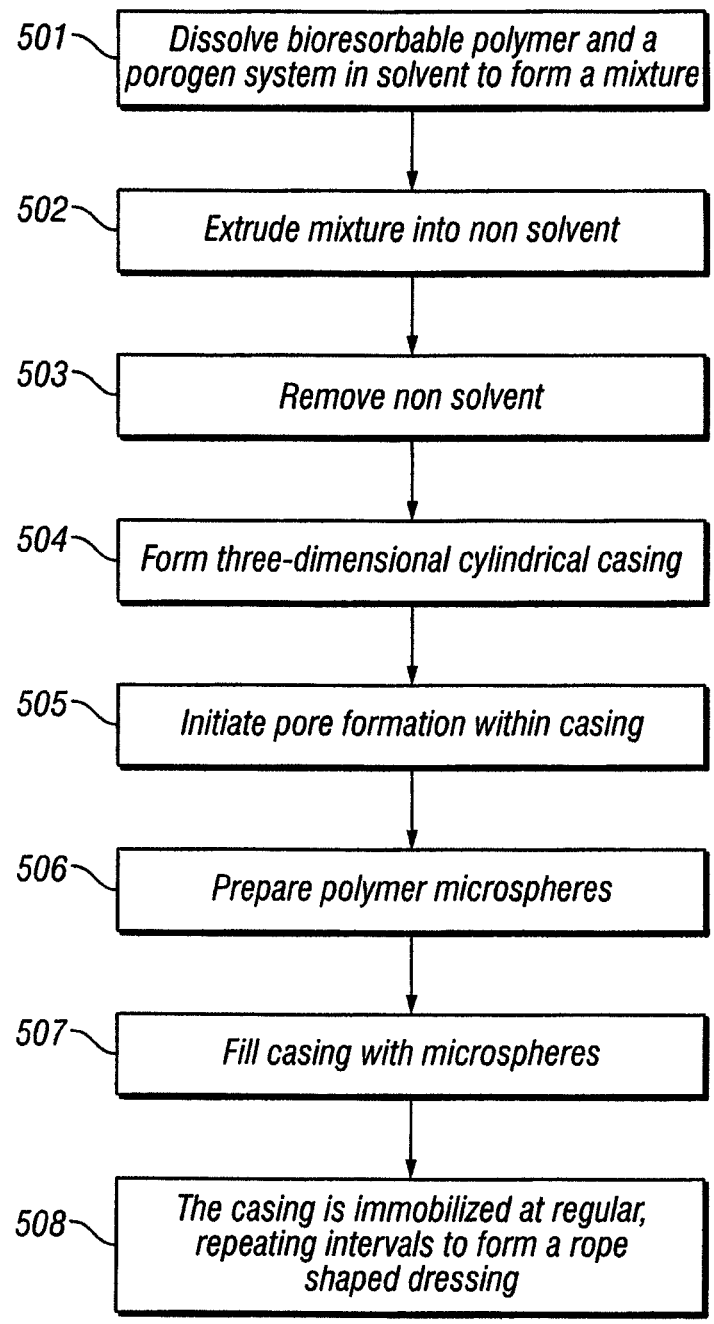
FIG. 5 illustrates a flowchart in accordance with some embodiments of the invention, demonstrating a process of making a porous bioresorbable comprising bioresorbable microspheres, where the dressing is made by extruded polymer.

A fifth embodiment in accordance with the invention is a method for preparing a porous bioresorbable dressing that can be placed into a wound of any size, shape or depth and be able to fill the wound completely because of its rope configuration, where the dressing is made by extruded polymer. The method of making the dressing is illustrated in FIG. 5. The dressing may be used to facilitate tissue growth and/or healing.

A bioresorbable polymer and a porogen system is dissolved in an appropriate solvent to form a non-solid mixture, such as a fluid or slurry, to form a mixture (501). Suitable polymers include, but are not limited to, polymers disclosed in the other embodiments of the invention. Further, the type of solvent used will depend upon the bioresorbable polymer(s) selected. In an alternate embodiment, the bioresorbable polymer is then mixed with one or more plasticizers.

The resulting mixture is then extruded into a non solvent for the polymer such that the mixture precipitates out of solution into a two-dimensional sheet shape (502). The residual non-solvent is removed (503). Examples of methods to remove the solvent include, but are not limited to, evaporation, oven drying, vacuum drying and the like. If one or more plasticizers is included in the mixture, then oven drying or vacuum drying may also be used as long as the conditions used do not favor evaporation of the plasticizer. If the polymer sheet contains undesired bubbles or an uneven thickness, the resultant polymer may also be heat pressed or compressed.

The resulting flat, two dimensional sheet of biodegradable polymer is then formed into a three dimensional casing by rolling the sheet into a cylinder shape and gluing the distal touching edges (504). Methods of gluing may include heat welding, chemical gluing, physical crimping, or any other means as long as edges are secured together to form the cylindrical shape. Further, the two-dimensional sheet may be cut or manipulated to better form the three-dimensional casing. For example, in one embodiment the sheet may have two ends patterned such that they are compatible for gluing or welding together. In another embodiment, the two-dimensional sheet is cut so that it has one edge having one or more slots and tongues comprising a catch or locking mechanism proximate the longitudinal edge thereof. The cylindrical casing is formed by inserting a portion of the tongue through the slot to provide a cylindrical casing. Further, the edges may be sealed by gluing.

The cylindrical dressing is then placed in water to react with the porogen system and create pores (505). The resulting spaces left by the porogen system result in a casing with pores. The size of the resulting pores is dependent upon the size of the porogen particles used. As such, one may use means to control the porogen particle size by use of, for example, sieving the particles with screens. Typically, the pore size produced by porogen system is about 5 to 1,500 microns. In one embodiment, the pore size is between about 100 and about 500 microns. In another embodiment, the pore size is between about 100 and about 250 microns. Further, the amount of porogen system used and the particle size of the porogen system will control the percent porosity. In one preferred embodiment, the percent porosity is at least about 50%. In another preferred embodiment, the percent porosity is about 70%. In yet preferred embodiment, the percent porosity is at least about 90%.

Bioresorbable polymer microspheres are then formed (506). The microspheres may be prepared by any means convenient to the practitioner. The diameter of the microspheres is preferably in the range of about 20 to about 800 microns range, more preferably about 400 microns to about 600 microns.

The cylindrical shaped biodegradable polymer, i.e., casing, is then filled with bioresorbable microspheres (507). The casing is constricted at regular, repeating intervals to form a rope shaped dressing. The constriction can occur by twisting, use of heat, solvent, or the like (508).

Figure 6:
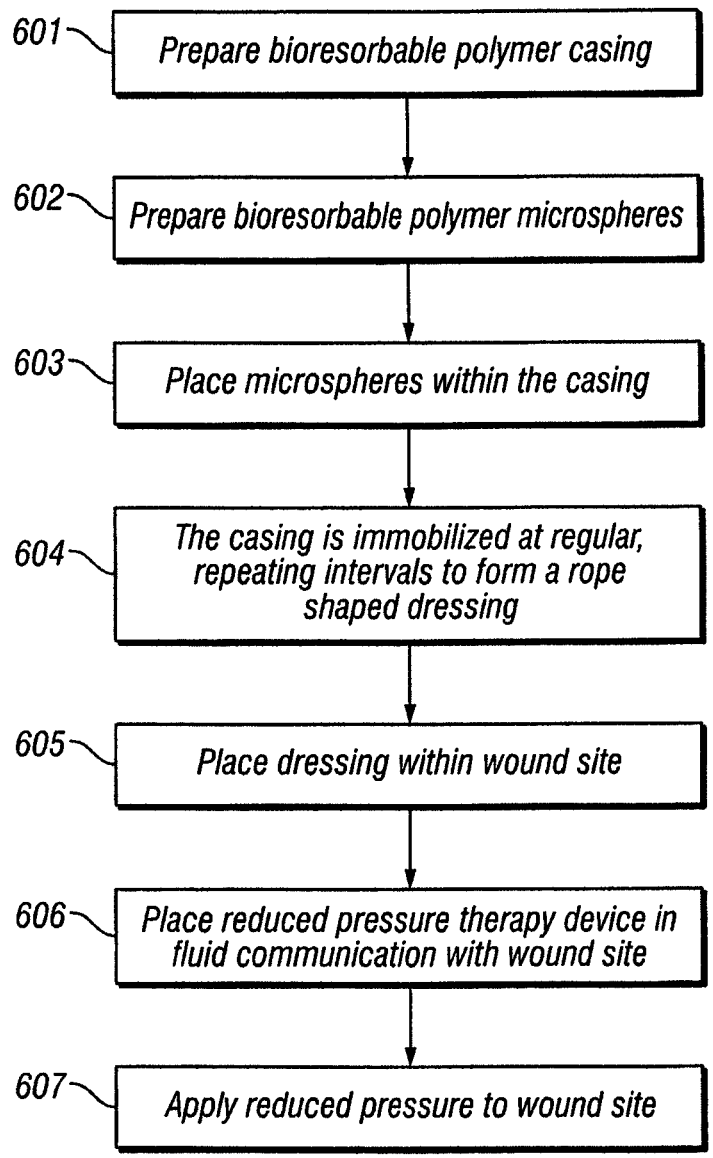
FIG. 6 illustrates a flowchart in accordance with some embodiments of the invention, demonstrating a process of facilitating tissue growth and/or healing by use of a reduced pressure delivery system with a bioresorbable dressing comprising bioresorbable microspheres.

The sixth embodiment in accordance with the invention is a method and apparatus for use of a reduced pressure delivery system to apply reduced pressure tissue treatment to a wound site, wherein the system includes a bioresorbable dressing comprising bioresorbable microspheres, as illustrated in FIG. 6. The dressing may be used to facilitate tissue growth and/or healing.

To start, a casing is formed by use of one or more bioresorbable polymers (601). The one or more bioresorbable polymers is dissolved in an appropriate solvent. The type of solvent used will depend upon the bioresorbable polymer(s) selected. The polymer mixture is then sprayed, dip coated or poured over a cylinder and the residual solvent is removed. Examples of methods to remove the solvent include, but are not limited to, evaporation, oven drying, vacuum drying and the like.

In an alternate embodiment, one or more plasticizers is added to the bioresorbable polymer in the solvent. If one or more plasticizers are included in the polymer, then the residual solvent may be removed by any method such as oven drying or vacuum drying as long as the conditions used do not favor evaporation of the plasticizer.

Bioresorbable polymer microspheres are then formed (602). The microspheres may be prepared by any means convenient to the practitioner. It is desired that the diameter of the microspheres be such that the microsphere packing within the casing does not impede the flexibility of the resulting dressing. Preferably, the microspheres have a diameter in the range of about 20 to about 800 microns range, more preferably about 400 microns to about 600 microns.

The polymer microspheres are then placed within the casing (603). The casing is constricted at regular, repeating intervals to form a rope shaped dressing. The constriction can occur by twisting, use of heat, solvent, or the like (604). The resulting dressing is then placed into the wound site to fill the shape and size of the wound (605). In an alternate embodiment, two or more dressings are braided or twisted together to form a thicker diameter dressing.

The reduced pressure therapy device is then placed in fluid communication with the wound site (606). Here, the wound site and the dressing are covered by a drape made of a flexible substance. Preferably, the drape is impermeable, thus blocking or slowing the transmission of either liquids or gas. Preferably, the drape is made of a material that permits the diffusion of water vapor but provides an air-tight seal over the wound site when reduced pressure therapy is applied. The drape will extend over the surface of the wound site and dressing and extend beyond the edges of the wound. The drape is secured to the skin surface about the wound circumference by, for example, adhesive material. At least one reduced pressure delivery tube is placed beneath the drape, and extends out from underneath the drape. The reduced pressure delivery tube may be made of any medical-grade tubing material, including without limitation paralyne-coated silicone or urethane. Further, the tubing may be coated with agents to prevent the tubing adhesion to the wound. For example, the tubing may be coated with heparin, anti-coagulants, anti-fibrogens, anti-adherents, anti-thrombinogens or hydrophilic substances. The reduced pressure delivery tube is placed in fluid communication to a reduced pressure source, which preferably comprises a canister safely placed under the vacuum through fluid communication with a reduced pressure source. Thus, in this embodiment, the dressing serves as a manifold to distribute the reduced pressure, assisting in applying reduced pressure to, delivering fluids to, or removing fluids from a wound site.

Reduced pressure therapy is then applied to the wound (607). It is understood that the frequency of reduced pressure treatment depends upon the location of the body, the size and shape of the wound site, the exact dressing or dressings used, and the types of various agents applied to the site, if any. Further, depending upon the treatment regiment, reduced pressure therapy may be substantially continuous application or cyclical such that it oscillates the pressure over time.

The unique configuration of the dressing described herein results in the microparticles providing resistance to the compression resulting form the reduced pressure therapy. This resistance to compression transmits mechanical forces to the wound, which aids in granular tissue formation. Over time, new tissue will grow into the spaces between the microparticles. Further, granulating tissue replaces the bioresorbable polymer as it degrades.

In an alternate embodiment, one or more plasticizers is added to the bioresorbable polymer in the solvent (601). If one or more plasticizers are included in the polymer, then the residual solvent may be removed by any method such as oven drying or vacuum drying as long as the conditions used do not favor evaporation of the plasticizer.

In still another embodiment, step (601) further comprises the addition of a porogen system to bioresorbable polymer in the solvent. Thus, when the dressing is placed within the wound site (605), wound fluids can react with the porogen system to initiate formation of pores in situ.

Figure 7:
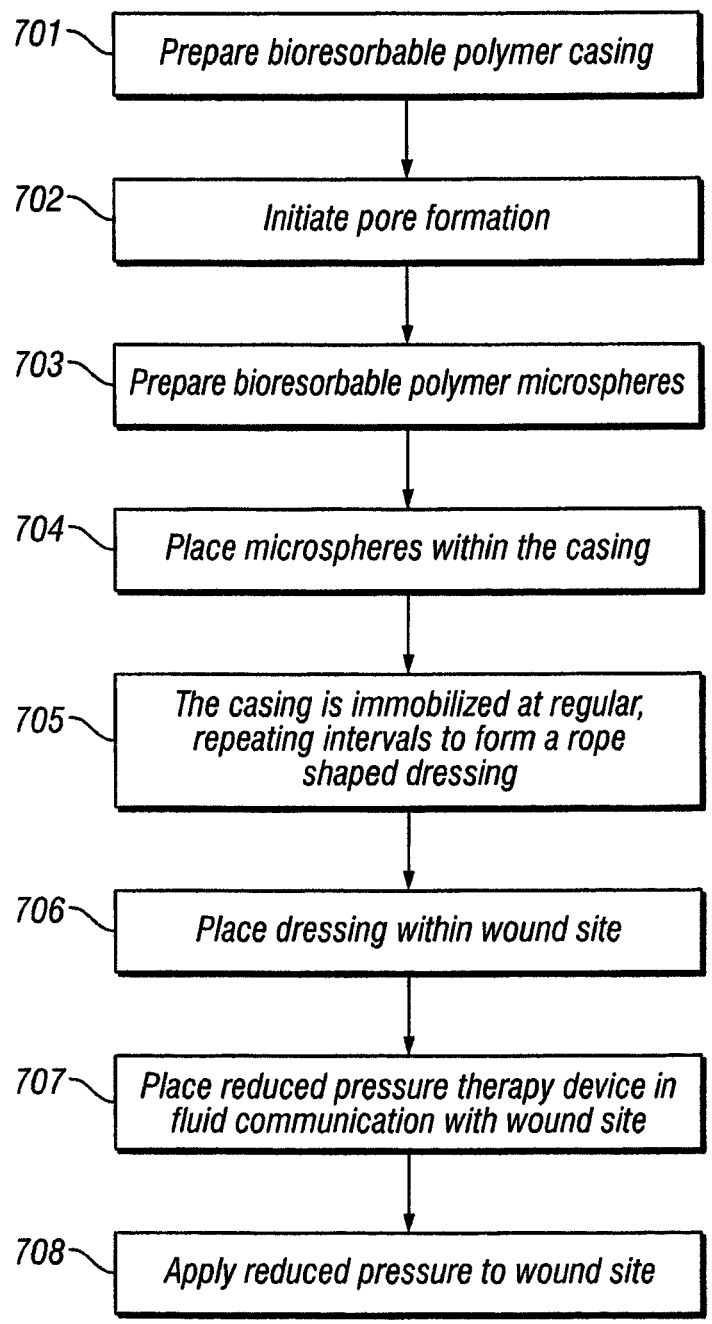
FIG. 7 illustrates a flowchart in accordance with some embodiments of the invention, demonstrating a process of facilitating tissue growth and/or healing by use of a reduced pressure delivery system with a porous bioresorbable dressing comprising bioresorbable microspheres.

The seventh embodiment in accordance with the invention is to a method and apparatus for a reduced pressure delivery system used to apply reduced pressure tissue treatment to a wound site, the system including a porous bioresorbable dressing comprising bioresorbable microspheres, as illustrated in FIG. 7.

A casing is formed by use of one or more bioresorbable polymers (701). The one or more bioresorbable polymers and a porogen system are dissolved in an appropriate solvent. The type of solvent used will depend upon the bioresorbable polymer(s) selected. The polymer mixture is then sprayed, dip coated or poured over a cylinder or within a hollow cylinder such that the surface is coated, and the residual solvent is removed by, for example, evaporation, oven drying, vacuum drying, and the like. In an alternate embodiment, one or more plasticizers is added to the bioresorbable polymer in the solvent. If one or more plasticizers are included in the polymer, then the method of residual solvent removal should not favor evaporation of the plasticizer.

The cylindrical casing is then placed in water to react with the porogen system (702). The resulting spaces left by the porogen system result in a casing comprising pores. The size of the resulting pores is dependent upon the size of the porogen particles used. As such, one may use means to control the porogen particle size by use of, for example, screens to sieve the particles. Typically, the pore size produced by porogen system is about 5 to 1,500 microns. In one embodiment, the pore size is between about 100 and about 500 microns. In another embodiment, the pore size is between about 100 and about 250 microns. Further, the amount of porogen system used and the particle size of the porogen system will control the percent porosity. In one preferred embodiment, the percent porosity is at least about 50%. In another preferred embodiment, the percent porosity is about 70%. In yet preferred embodiment, the percent porosity is at least about 90%.

Bioresorbable polymer microspheres are then formed (703). The microspheres may be prepared by any means convenient to the practitioner. It is desired that the diameter of the microspheres be such that the microsphere packing within the casing does not impede the flexibility of the resulting dressing. Further, the diameter of the microspheres should be greater than the diameter of the pores within the casing formed by the porogen system. Preferably, the microspheres have a diameter in the range of about 20 to about 800 microns range, more preferably about 200 microns to about 600 microns.

The polymer microspheres are then placed within the casing (704). The cylindrical casing is constricted at regular intervals (705). The constriction means may be, but is not limited to, twisting the casting, use of heat, solvent, or the like, to form a dressing. The resulting dressing is then placed within the wound such that it fills the shape and size of the wound (706). In an alternate embodiment, two or more dressings are braided or twisted together to form a thicker diameter dressing.

The reduced pressure therapy device is then placed in fluid communication with the wound site (707). Here, the wound site and the dressing are covered by a drape made of an impermeable substance that is flexible. The drape will extend over the surface of the wound site and dressing and extend beyond the edges of the wound, and be preferably secured to the skin surface about the wound circumference. At least one reduced pressure delivery tube is placed beneath the drape, and extends out from underneath the drape. The reduced pressure delivery tube is placed in fluid communication to a reduced pressure source, which preferably comprises a canister safely placed under the vacuum through fluid communication with a reduced pressure source. Thus, in this embodiment, the dressing serves as a manifold to distribute the reduced pressure.

Reduced pressure therapy is then applied to the wound (708). The unique configuration of the dressing described therein results in the microparticles providing resistance to the compression resulting form the reduced pressure therapy. This resistance to compression transmits mechanical forces to the wound, which aids in granulation tissue formation. Over time, new tissue will grow into the spaces between the microparticles. Further, granulating tissue replaces the bioresorbable polymer as it degrades.

Figure 8:
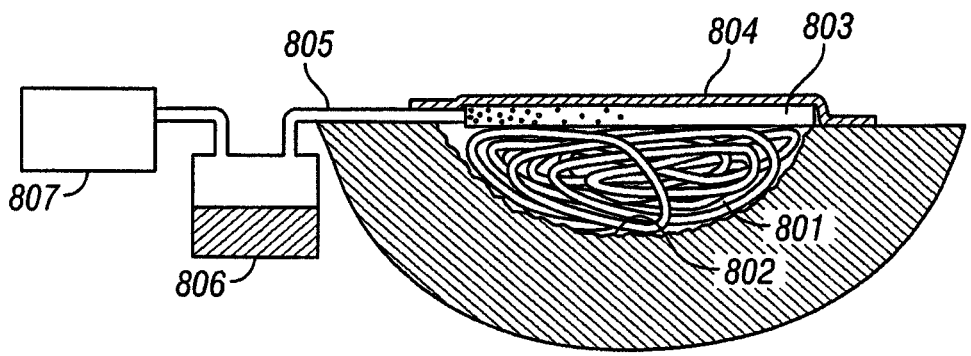
FIG. 8 illustrates a graphical representation of an apparatus for inducing new tissue growth and/or healing at a wound site by use of a bioresorbable polymer dressing comprising bioresorbable microspheres with a reduced pressure delivery system.

An eighth embodiment is to a method and apparatus for inducing new tissue growth at a wound site by use of a bioresorbable polymer dressing comprising bioresorbable microspheres contained within a bioresorbable casing, as illustrated in FIG. 8. Here, a dressing (801) made by the methods disclosed herein and illustrated within FIGS. 1-5, 10A, 10B, and 10C is placed within a wound site (802) by coiling the dressing (801) such that it fills the shape, size and depth of the wound site (802).

The wound site (802) and dressing (801) are then covered by a distribution manifold (803). A drape (804) is placed over the surface of the wound site (801), dressing (802) and distribution manifold (803) and extended beyond the edges of the wound site, where it is then secured to the skin surface about the wound circumference by, for example, an adhesive. Preferably, the drape (804) is made of an impermeable substance that is flexible and permits the diffusion of water vapor but provides an air-tight enclosure.

The distribution manifold (803) comprises at least one reduced pressure delivery tube (805) that is fluidly connected to the manifold (803). Within the distribution manifold, the reduced pressure delivery tube (805) is perforated by one or more holes. Outside of the distribution manifold, the reduced pressure delivery tube (805) is non-perforated and extends from the dressing (803) and out from the drape (804). The reduced pressure delivery tube (805) may be made of any medical-grade tubing material, including without limitation paralyne-coated silicone or urethane, and may be coated with agents to prevent the tubing (805) adhesion to the wound site.

The reduced pressure delivery tube (805) is placed in fluid communication to a reduced pressure source(806), which preferably comprises a fluid collection container (806) safely placed under the vacuum through fluid communication with a reduced pressure source. Thus, when the reduced pressure source (806) is turned on, reduced pressure is applied to the wound site (802). Upon application of reduced pressure, the drape (804) compresses and conforms to the surface of the distribution manifold (803), which applies pressure to the dressing (801), mechanically compressing the dressing (801) and pressing the dressing (801) into the wound site (802). Further, the reduced pressure may draw wound fluids present at the wound site (802) through the distribution manifold (803) and reduced pressure delivery tube (805) to be deposited in the fluid collection container (806), thereby preventing fluids from entering the reduced pressure source (807) itself. Thus, in this embodiment, the distribution manifold serves to distribute the reduced pressure.

In one embodiment, the system and method of FIG. 8 may also be used with a rope-shaped bioresorbable dressing comprising bioresorbable microspheres, where the casing does not contain pores.

In another embodiment, the system and method of FIG. 8 is used with a dressing comprises a casing with pores. Here, the casing is formed of bioresorbable polymers and a porogen system, where the casing is exposed to a fluid which reacts with the porogen in the casing, creating pores. The porous casing is then filled with bioresorbable microparticles, constricted at regular, repeating intervals to form a rope shaped dressing, and then is placed within the wound site.

In still another embodiment, the system and method of FIG. 8 is used with a casing comprises a porogen system, but the porogen system is not activated in advance of the dressing being placed within the wound site. In this embodiment, the porogen system within the casing of the dressing reacts with wound fluids, thereby forming pores within the casing in situ.

Figure 9:
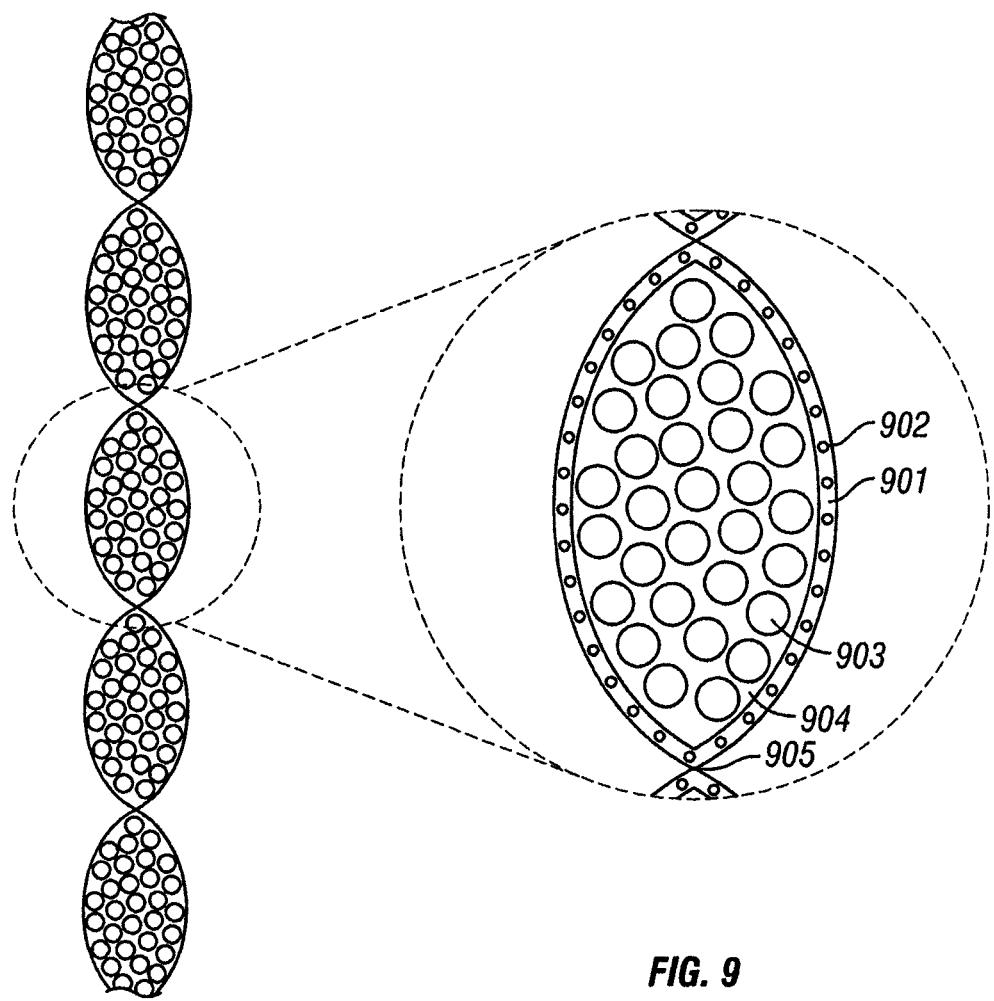
FIG. 9 illustrates a graphical representation of a porous bioresorbable dressing comprising bioresorbable microspheres.

An example configuration of a porous bioresorbable dressing comprising bioresorbable microparticles is shown in FIG. 9. The casing (901) of the dressing is made of a bioresorbable polymer, and preferably includes a plasticizer. Pores in the casing (902) are formed by use of a porogen system. The casing (901) is filled with bioresorbable polymer microspheres (903), which may be prepared by any means convenient to the practitioner. The diameter of the microspheres (903) should be greater than the diameter of the pores (902) within the casing. Further, the diameter of and the amount of microspheres used will result in altering the void space within the microspheres (904). The void space is important because new tissue will infiltrate the void space before the bioresorbable microspheres break down. Further, the diameter of and the amount of the microspheres used should be such that the resulting dressing is flexible enough to coil within the wound site.

Figure 10A:
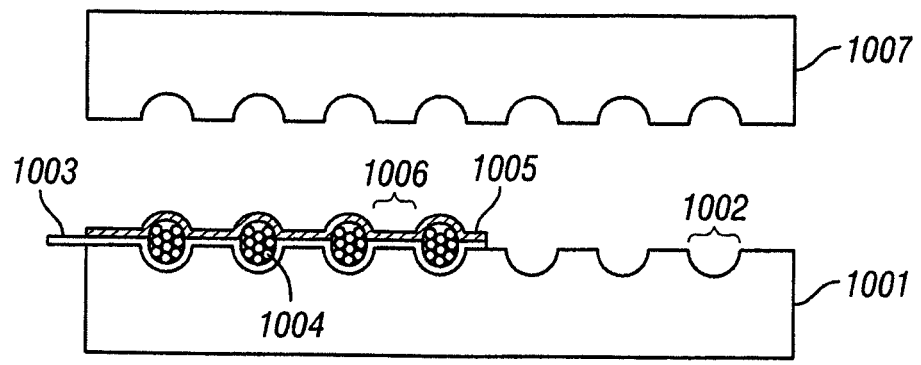
FIG. 10 A-C illustrates graphical representations of mold configurations used to prepare a bioresorbable capsule linked dressing.

Another embodiment of the invention is to use of a mold to form a bioresorbable dressing comprising bioresorbable microparticles, whereas the mold is illustrated in FIG. 10A. First, a two-dimensional film of bioresorbable polymer is formed. The two-dimensional film may be formed by any means. For example, the bioresorbable polymer may be dissolved in an appropriate solvent and then sprayed, or poured into a two dimensional sheet mold where the residual solvent is removed. Alternatively, the bioresorbable polymer may be dissolved into an appropriate solvent and then extruding into a non-solvent. Further, the resulting bioresorbable polymer film may be heat pressed or compressed to form the film into a desired thickness. To make the film more malleable, one or more plasticizers may added to the bioresorbable polymer in the solvent.

The resulting first bioresorbable polymer film (1003) is then placed into a mold (1001). The mold is a three-dimensional structure comprising craters or hollows (1002) placed on one face of the mold. An alternative view of the craters of the mold is presented in FIG. 10B. The first biodegradable polymer film (1003) is placed over the mold such that the film is compressed into and contacts the inner surface of the craters or hollows (1002).

Bioresorbable polymer microspheres are then formed (1004). The microspheres may be prepared by any means convenient to the practitioner. For example, the microsphere preparation method may be a spraying method, oil-in-water emulsion, water-in-oil emulsion, oil-in-oil emulsion method, and the like. Preferably, the microspheres formed have a diameter in the range of about 20 to about 800 microns range, more preferably about 400 microns to about 600 microns.

The bioresorbable polymer microspheres are then placed within the craters (1002) and a second bioresorbable polymer film (1005) is placed over the microspheres (1004) and first bioresorbable polymer film (1003). Thus the first bioresorbable polymer film (1003) and second bioresorbable polymer film (1005) contact each other at the area (1006) about the circumference of the craters. A second mold (1007) is placed on top of the second bioresorbable polymer film (1005) and the two molds (1001) and (1007) are hot pressed together to seal the microspheres within the craters, thereby resulting a bioresorbable linked capsules dressing.

Further, in one alternate embodiment, a bioresorbable suture may be used to assist in linking the bioresorbable capsules. Thus, the first mold (1001) will comprise a first bioresorbable polymer film (1003) placed within the craters (1002) and the craters (1002) filled with microspheres (1004). A bioresorbable suture is then laid across the mold such that the suture lies over the craters (1002). A second bioresorbable polymer film (1005) placed over the suture, microspheres (1004) and first bioresorbable polymer film (1003). The second bioresorbable polymer film (1005) may then be held in place, to prevent the microspheres (1004) from falling out, and the first mold inverted onto the second mold (1007). The two molds (1001) and (1007) are then hot pressed together to seal the microspheres within the craters, thereby resulting linked bioresorbable capsules. In addition, it is contemplated that the two molds (1001) and (1007) may also be formed to accommodate the suture by including a hollowed channel (1008) placed between the craters (1002), as illustrated in an alternate view of the mold (1001) in FIG. 10C. Thus, in this alternate view, the area (1006) between the craters (1002) would have a hollow channel (1008) such that when the first mold (1001) and second mold (1007) are hot sealed together, the suture is not damaged or flattened.

In yet another alternate embodiment, the second mold (1007) also comprises a third bioresorbable polymer film placed within craters of the second mold and filled with bioresorbable polymer microspheres. Thus, the first mold (1001) will comprise a first bioresorbable polymer film (1003) placed within the craters (1002), craters (1002) filled with microspheres (1004), and a second bioresorbable polymer film (1005) placed over the microspheres (1004) and first bioresorbable polymer film (1003). The second bioresorbable polymer film (1005) may then be held in place, to prevent the microspheres (1004) from falling out, and the first mold inverted onto the second mold (1001). The two molds (1001) and (1007) are then hot pressed together to seal the microspheres within the craters, thereby resulting in a linked bioresorbable capsules dressing.

Further, in yet another alternate embodiment, the bioresorbable polymer films further comprises a porogen system. As such, the bioresorbable polymer films may be placed in water to react with the porogen system and create pores. This may occur before the bioresorbable films are used to form linked capsules by use of the mold of FIG. 10A-C. Alternatively, the reaction of the porogen system and creation of pores may occur in situ when the linked bioresorbable capsule dressing comes in contact with wound fluids. The size of the resulting pores is dependent upon the size of the porogen particles used. As such, one may use means to control the porogen particle size by use of, for example, sieving the particles with screens before the porogen particles are added to the bioresorbable polymer. Typically, the pore size produced by porogen system is about 5 to 1,500 microns. In one embodiment, the pore size is between about 100 and about 500 microns. In another embodiment, the pore size is between about 100 and about 250 microns. Further, the amount of porogen system used and the particle size of the porogen system will control the percent porosity. In one preferred embodiment, the percent porosity is at least about 50%. In another preferred embodiment, the percent porosity is about 70%. In yet preferred embodiment, the percent porosity is at least about 90%.

It is desired that the diameter of the microspheres be such that the pores from the casing are smaller than the microsphere diameter. It is undesirable to have the diameter of the microspheres be smaller than the casing pore size because the microspheres would not remain within the casing.

Figure 10B:
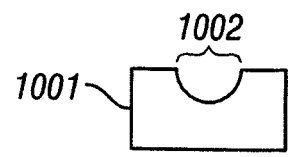
Figure 10C:
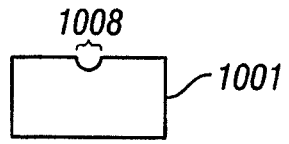
Figure 11:
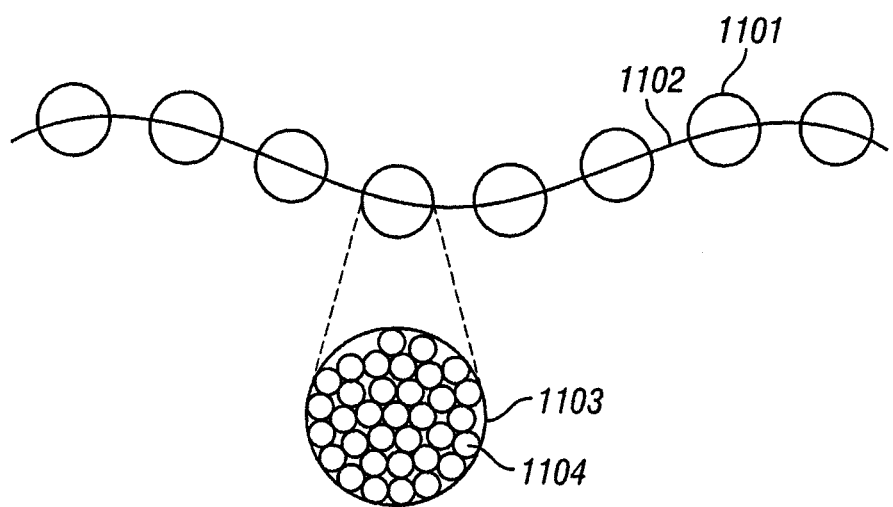
FIG. 11 illustrates a graphical representation of a bioresorbable capsule linked dressing formed by use of the molds of FIG. 10 A-C.

The use of the molds of FIG. 10A-10C therefore result in the dressing illustrated in FIG. 11. Here, bioresorbable capsules (1101) are linked together by a bioresorbable material (1102) formed from either use of a bioresorbable suture or compression of bioresorbable polymer films. Thus, each capsule (1101) is formed of bioresorbable microparticles (1104) enclosed within a bioresorbable polymer film (1103).

The dressing of FIG. 11 may be used with reduced pressure therapy. This dressing has the novel benefit in that it can coil with a wound site and fill the shape, size and depth of the wound site. When reduced pressure therapy occurs, the capsules (1101) compress into the wound site, assisting in granulation. Because of the pockets of air between the capsules, the dressing may be used by itself to distribute reduced pressure during the therapy. Alternatively, the dressing of FIG. 11 may be used with a distribution manifold.

Another embodiment of the invention is to a tissue growth kit is provided for promoting new tissue growth at a wound site. The tissue growth kit includes a rope-shaped bioresorbable dressing comprising bioresorbable microparticles, a manifold adapted to contact the dressing, and a reduced pressure device.

Further, in a final embodiment of the invention, a bioresorbable dressing comprising bioresorbable microparticles may be formed whereby a bioresorbable polymer casing or film is not used. In this embodiment, microparticles are formed and then dried. The microparticles are placed within a cylindrical mold that is not made of a bioresorbable material. The microparticles are cross linked in the dry or hydrated state by any means, including but not limited to, photo linking, chemical linking, thermal linking, and the like. The mold is removed, and the resulting cross linked microparticles form a cylindrically-shaped dressing comprising microparticles. The dressing may then be used to assist in reduced pressure therapy.

While many of the embodiments described herein include microspheres having a substantially spherical shape, it should be appreciated that microparticles having alternative shapes could be substituted for microspheres. For example, microparticles of other shapes could also be formed. The microparticles may be rectangular parallelepiped, cylindrical, rod-shaped, cuboidal, irregular, or any other shape.

It should also be understood that any bioresorbable film may be used as a casing for the microparticles. Examples may include, without limitation, woven, non-woven, or knitted mats or sheets. It is generally desirable that these materials be flexible and porous and further capable of containing the microparticles.

It should be apparent from the foregoing that an invention having significant advantages has been provided. While the invention is shown in only a few of its forms, it is not just limited but is susceptible to various changes and modifications without departing from the spirit thereof.

We claim:

1. A system for applying reduced pressure tissue treatment to a wound site, the system comprising:
   a dressing that is porous bioresorbable and comprising a rope shaped casing having microparticles inside the casing that are bioresorbable, constrictions at repeating intervals of the rope shaped casing, and having a porogen system in the casing adapted to form pores in the casing, the dressing adapted to be disposed adjacent the wound site;
   a drape adapted to cover the dressing and create a sealed space containing the dressing;
   a reduced pressure source adapted to supply reduced pressure; and
   a reduced pressure delivery tube adapted to be fluidly coupled between the reduced pressure source and the dressing to provide the reduced pressure to the dressing.

2. The system of claim 1, further comprising a distribution manifold fluidly coupled to the reduced pressure delivery tube to distribute the reduced pressure.

3. The system of claim 2, wherein the distribution manifold compresses the dressing against the wound site.

4. The system of claim 1, wherein the casing comprises a substantially cylindrical shape.

5. The system of claim 1, wherein the casing comprises a substantially cylindrical shape and the microparticles are disposed within the casing.

6. The system of claim 1, wherein the porogen system forms the pores in the casing in response to contact with a fluid.

7. The system of claim 6, wherein the fluid comprises a body fluid.

8. The system of claim 6, wherein the fluid comprises water.

9. The system of claim 1, wherein the porogen system comprises sodium carbonate and an acid.

10. The system of claim 1, wherein the porogen system comprises a salt.

11. The system of claim 1, wherein a size of the microparticles is between about 400 and about 600 microns.

12. The system of claim 1, wherein the microparticles comprise a PLA:PCL (poly(lactide):polycaprolactone) copolymer.

13. The system of claim 12, wherein the ratio of PLA:PCL is about 90:10.

14. The system of claim 12, wherein the ratio of PLA:PCL is about 80:20.

15. The system of claim 1, wherein the microparticles comprise microspheres.

16. The system of claim 1, wherein the casing has a porosity between about 50% and about 90%.

17. The system of claim 1, wherein the casing has a porosity greater than about 70%.

18. The system of claim 1, wherein the casing has a porosity of about 50%.

19. The system of claim 1, wherein a diameter of the pores of the casing is between about 100 microns and about 500 microns.

20. The system of claim 1, wherein a size of the microparticles is greater than a diameter of the pores.

21. The system of claim 1, wherein the casing further comprises a plasticizer.

22. The system of claim 1, wherein the dressing comprises a first dressing, the system further comprising a second dressing twisted together with the first dressing.

23. The system of claim 1, wherein the dressing comprises a first dressing, the system further comprises a second dressing braided together with the first dressing.

* * * * *